(12) United States Patent
Madabhushi et al.

(10) Patent No.: US 10,902,591 B2
(45) Date of Patent: Jan. 26, 2021

(54) PREDICTING PATHOLOGICAL COMPLETE RESPONSE TO NEOADJUVANT CHEMOTHERAPY FROM BASELINE BREAST DYNAMIC CONTRAST ENHANCED MAGNETIC RESONANCE IMAGING (DCE-MRI)

(71) Applicant: Case Western Reserve University, Cleveland, OH (US)

(72) Inventors: Anant Madabhushi, Shaker Heights, OH (US); Nathaniel Braman, Cleveland, OH (US); Andrew Janowczyk, East Meadow, NY (US); Kavya Ravichandran, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 65 days.

(21) Appl. No.: 16/268,652

(22) Filed: Feb. 6, 2019

(65) Prior Publication Data

US 2019/0251688 A1 Aug. 15, 2019

Related U.S. Application Data

(60) Provisional application No. 62/628,567, filed on Feb. 9, 2018.

(51) Int. Cl.
*G06K 9/00* (2006.01)
*G06T 7/00* (2017.01)
(Continued)

(52) U.S. Cl.
CPC .............. *G06T 7/0012* (2013.01); *G06K 9/46* (2013.01); *G06K 9/4642* (2013.01); *G06K 9/628* (2013.01);
(Continued)

(58) Field of Classification Search
None
See application file for complete search history.

(56) References Cited

U.S. PATENT DOCUMENTS

2014/0270451 A1* 9/2014 Zach ...................... A61B 5/055
382/131
2015/0087967 A1* 3/2015 Springer, Jr. .... G01R 33/56366
600/419

(Continued)

*Primary Examiner* — Hadi Akhavannik
(74) *Attorney, Agent, or Firm* — Eschweiler & Potashnik, LLC

(57) ABSTRACT

Embodiments access a pre-neoadjuvant chemotherapy (NAC) radiological image of a region of tissue demonstrating breast cancer (BCa), the region of tissue including a tumoral region, the image having a plurality of pixels; extract a set of patches from the tumoral region; provide the set of patches to a convolutional neural network (CNN) configured to discriminate tissue that will experience pathological complete response (pCR) post-NAC from tissue that will not; receive, from the CNN, a pixel-level localized patch probability of pCR; compute a distribution of predictions across analyzed patches based on the pixel-level localized patch probability; classify the region of tissue as a responder or non-responder based on the distribution of predictions, and display the classification. Embodiments may further generate a probability mask based on the pixel-level localized patch probability; and generate a heatmap of likelihood of response to NAC based on the probability mask and the pre-NAC radiological image.

21 Claims, 12 Drawing Sheets

(51) Int. Cl.
*G06T 5/50* (2006.01)
*G06K 9/46* (2006.01)
*G06K 9/62* (2006.01)
*G16H 30/40* (2018.01)
*G06N 3/08* (2006.01)
*G06N 7/00* (2006.01)

(52) U.S. Cl.
CPC ......... *G06K 9/6228* (2013.01); *G06K 9/6267* (2013.01); *G06N 3/08* (2013.01); *G06N 7/005* (2013.01); *G06T 5/50* (2013.01); *G16H 30/40* (2018.01); *G06K 2209/05* (2013.01); *G06T 2207/10088* (2013.01); *G06T 2207/20072* (2013.01); *G06T 2207/20076* (2013.01); *G06T 2207/20084* (2013.01); *G06T 2207/30068* (2013.01); *G06T 2207/30096* (2013.01)

(56) References Cited

U.S. PATENT DOCUMENTS

| | | | |
|---|---|---|---|
| 2015/0347679 A1* | 12/2015 | Varadan | G16C 20/30 424/133.1 |
| 2016/0155225 A1* | 6/2016 | Madabhushi | G06T 7/0012 382/131 |
| 2017/0039737 A1* | 2/2017 | Madabhushi | A61B 5/08 |
| 2017/0071496 A1* | 3/2017 | Gillies | A61B 5/0263 |
| 2018/0033138 A1* | 2/2018 | Prasanna | G06T 7/0012 |

* cited by examiner

|  | pCR | non-pCR |
|---|---|---|
| Number | 49 | 118 |
| Average Age (years) | 46.84 | 48.54 |
| Survived | 45 | 89 |
| Average Largest Diameter (mm) | 63.44 ± 27.00 | 69.25 ± 20.50 |
| Receptor Status | | |
| HER2 Positive | 25 | 28 |
| Hormone Receptor Positive, Her2 Negative | 7 | 59 |
| Triple Negative | 15 | 28 |

Figure 2

PREDICTING PATHOLOGICAL COMPLETE RESPONSE TO NEOADJUVANT CHEMOTHERAPY FROM BASELINE BREAST DYNAMIC CONTRAST ENHANCED MAGNETIC RESONANCE IMAGING (DCE-MRI)

CROSS REFERENCE TO RELATED APPLICATIONS

This application claims the benefit of U.S. Provisional Application 62/628,567 filed Feb. 9, 2018, which is incorporated by reference herein in its entirety.

FEDERAL FUNDING NOTICE

This invention was made with government support under the grant(s): F31CA221383-01A1, R21CA167811-01, R21CA179327-01, R21CA195152-01, U24CA199374-01, and R01DK098503-02, awarded by the National Institutes of Health. The government has certain rights in the invention.

BACKGROUND

Neoadjuvant chemotherapy (NAC) is used to treat breast cancer (BCa) tumors prior to invasive surgery since it increases surgical options. Pathological complete response (pCR), i.e., the absence of residual invasive disease in the breast or lymph nodes, is used as a metric for the efficacy of NAC. However, existing approaches, including current imaging and clinical metrics, are not sufficiently accurate for predicting eventual pCR from data acquired prior to NAC. Treatment response can currently, using existing approaches, only be assessed by comparing dynamic contrast enhanced magnetic resonance imaging (DCE-MRI) acquired before and after an initial NAC treatment period. For the ten to fifty percent of BCa patients who will not respond to NAC treatment, this preliminary treatment represents a window of ineffective and unnecessary chemotherapy, which can potentially result in metastasis, since other, more effective treatments may be delayed while the ineffective treatment is administered. Thus, a more accurate, non-invasive approach to predicting pCR in BCa patients prior to NAC would be advantageous.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

FIG. 2 illustrates a table describing a dataset used to train and test an exemplary CNN to predict pCR.

DETAILED DESCRIPTION

Figure 1:
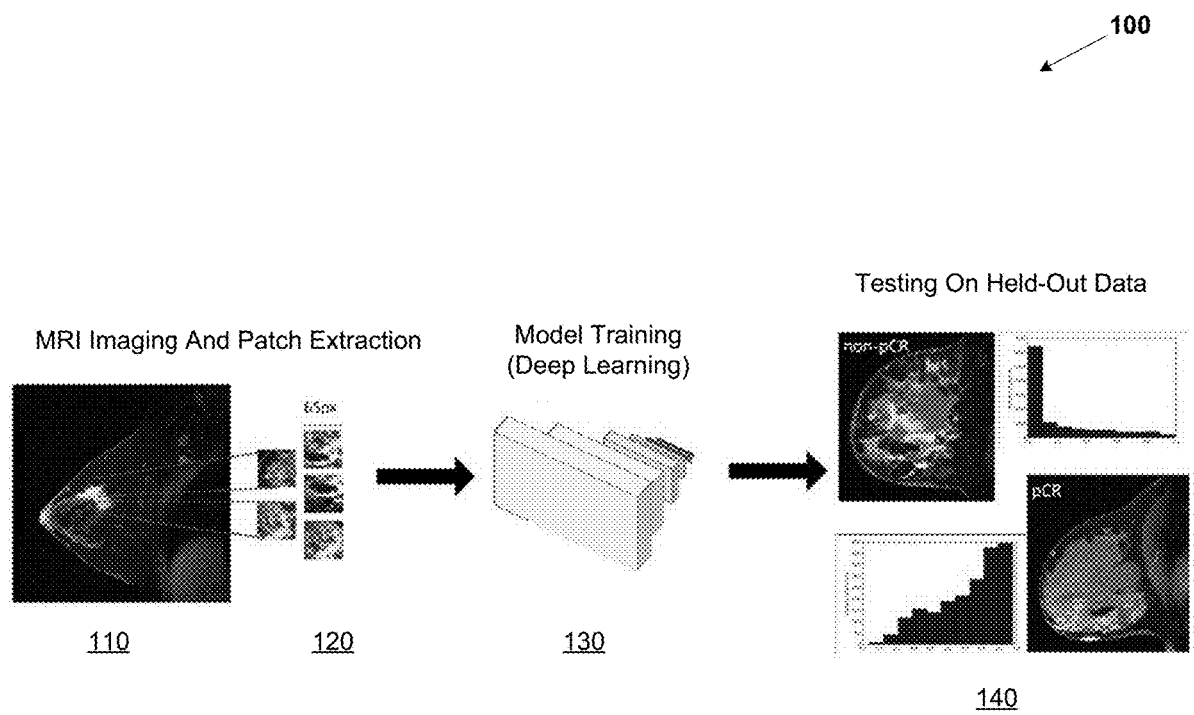
FIG. 1 illustrates an example workflow for predicting pCR from DCE-MRI imagery with a convolutional neural network (CNN).

Neoadjuvant chemotherapy (NAC) is used to treat breast tumors in breast cancer (BCa), prior to invasive surgery, since NAC may increase surgical options. Pathological complete response (pCR), defined as the absence of residual disease in the breast or lymph nodes, is used as a metric for the efficacy of NAC. However, existing imaging and clinical metrics are not sufficiently accurate for prediction of pCR prior to NAC. Using existing approaches, treatment response can only be assessed by comparing dynamic contrast-enhanced magnetic resonance imaging (DCE-MRI) imagery acquired before and after an initial NAC treatment period. However, ten to fifty percent of BCa patients will not respond to NAC, and thus this preliminary treatment represents a window of ineffective and unnecessary chemotherapy that those ten to fifty percent of BCa patients might otherwise be spared. Furthermore, the period of time wasted on ineffective treatment may potentially result in metastasis.

Deep learning, including the use of artificial neural networks arranged in layers applied to learning tasks, may be employed to develop models to draw conclusions (i.e., classify) from images, especially when it is not known what types of features to investigate. In particular, CNNs may converge to features that combine lower level abstractions (e.g., edge detection) to higher order features which maximally discriminate between classes of interest (e.g., responder, non-responder). In contrast, traditional approaches to using machine learning to predict pCR involve domain-driven hand-crafted feature development rather than unsupervised feature discovery.

For example, one existing approach to predicting pCR post-NAC in breast cancer repurposes an existing CNN that has been trained for another purpose (e.g., to discriminate objects in non-medical imagery), to extract features from MRI imagery. This existing approach then uses those extracted features to feed a second machine learning classifier, in this case, a support vector machine (SVM), to make a classification based on the extracted features. In this existing approach, the CNN is not actually learning or tailored to the task of predicting pCR. Instead, the CNN is outputting features optimized for the original purpose of identifying objects in non-medical images that just happen to have some predictive value with respect to pCR when later provided to an SVM. Furthermore, in this existing approach, increasing the size of a training data set is unlikely to improve predictive performance or offer any additional medical insight from the imagery.

In contrast, embodiments employ a CNN specifically trained to predict response, including pCR, from end-to-end. Embodiments employing a CNN that is trained from scratch improve on existing approaches by ensuring that each level of the CNN is tailored towards predicting response or non-response. Embodiments may ensure that each level of the CNN is tailored towards predicting pCR or non-pCR. Embodiments are unconstrained by a limited set of pre-defined features, and facilitate the identification of features in an unsupervised fashion that optimally distinguish disease states (e.g., pCR, non-pCR). Embodiments thus may be further refined by applying additional training data to train the CNN, resulting in increased accuracy in identifying patterns explicitly associated with therapeutic outcome.

Additionally, some existing approaches use an indirect measurement of response, for example, grouping patients into categories based on length of survival after chemotherapy. This existing approach is not necessarily predictive of response, since there may be many reasons a patient has long or short term survival that are unrelated to the efficacy of chemotherapy. Thus, the benefit of existing approaches to guiding therapy is limited. In contrast, embodiments described herein consider a direct treatment endpoint: pCR (i.e., the elimination of invasive cancer from a patient's surgical sample following chemotherapy). Predicting changes in tumor extent as described herein has the clinical impact of facilitating the improved assessment and guidance of surgical options earlier, since patients with significantly reduced tumors may be more eligible for minimally invasive surgery.

Embodiments consider pre-treatment imagery of tissue demonstrating cancerous pathology with an end-to-end CNN approach to produce a map of predictive regions within the tumoral region. There are currently no existing approaches for predicting pCR from before a patient receives NAC, either through imaging or genomic or pathological testing. Embodiments predict pCR from pre-treatment imagery and thus facilitate the focusing of resources on those patients who will respond to NAC prior to them receiving NAC, and prioritize other treatment options for those patients who will not respond to NAC, thus reducing the risk of adverse chemotherapeutic side-effects and metastasis. Embodiments thus further facilitate using fewer resources, including physician time, and expensive chemotherapy agents.

Figure 4:
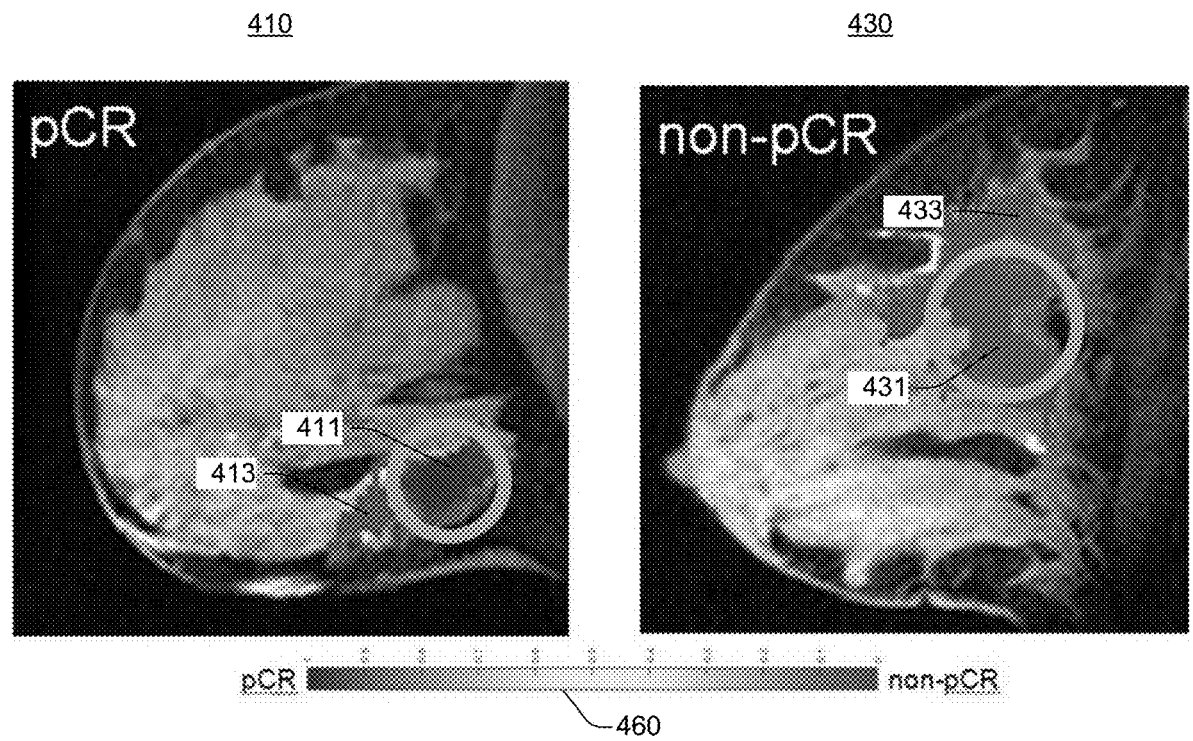
FIG. 4 illustrates regions within a tumor region that are predictive of response.

Embodiments employ a deep learning classifier that uses DCE-MRI imagery to predict whether or not a patient will respond to chemotherapy, including NAC. Embodiments may train the deep learning classifier using a training dataset and a testing dataset. Embodiments extract patches from within a tumor region represented in the DCE-MRI imagery, and pass the patches as training data, testing data, or clinical data, to a convolutional neural network (CNN). The probabilities output by the CNN represent the probability that a given patch belongs to a given class (e.g., likely to experience response or unlikely to experience response, likely to experience pCR or unlikely to experience pCR). Embodiments compute a distribution of probabilities across the analyzed patches. The probabilities may then be used to generate a probability mask of the image. Embodiments may further generate a heatmap based on the probability mask and the image. Embodiments may further identify, based on the correlation between patches extracted from the tumoral region and response to NAC, which specific areas of the tumor are most predictive of overall response. For example, FIG. 4 illustrates DCE-MRI images 410 and 430. DCE-MRI image 410 is of a region of tissue that experienced pCR. DCE-MRI image 430 is of a region of tissue that did not experience pCR. Region 411 indicates a region of high predictive value in a tumoral region, while region 413 indicates a region of lower predictive value. Region 431 indicates a region of high predictive value in a tumor region, while region 433 indicates a region of lower predictive value. A legend 460 is also illustrated. Embodiments employ this spatial localization to facilitate the generation of a spatial map of the most predictive regions, which further facilitates the guiding of tissue biopsies or other surgical procedures based on the spatial map.

One example embodiment is now described in detail. FIG. 1 illustrates an exemplary workflow 100 corresponding to this example embodiment. In this embodiment 167 patients who had received DCE-MRI imaging prior to NAC treatment and who had undergone surgery following NAC were selected from the multi-site Investigation of Serial Studies to Predict Your Therapeutic Response with Imaging and Molecular Analysis (I-SPY1 TRIAL) data set from The Cancer Imaging Archive (TCIA). A set of images, including pre-contrast and at least two post-contrast phases of DCE-MRI were accessed of each of the 167 patients. Of the selected 167 patients, 49 patients achieved pCR to NAC while the remaining 118 patients did not (i.e., were non-pCR). In this example, DCE-MRI scans, including pre-contrast phase and post-contrast phase imagery, were collected prior to treatment using an MRI system that included a 1.5 T magnet and dedicated four or eight channel breast radio frequency coils in the sagittal plane. FIG. 2 includes table 200 which describes properties of the 167 selected patients including average age, number of survivors, average largest diameter, and receptor status. In another embodiment, other patient datasets may be employed to train and test the CNN.

Embodiments may pre-process the set of images. A member of the set of images includes a tumoral region, and may also include non-tumoral (i.e., stroma) tissue. MRI signal values may vary significantly between scanners in a way that does not reflect any biological or physical meaning in the tissue being scanned. The intensity of each pixel in a member of the set of images is normalized to the mean intensity of a reference region of the stroma or other non-tumor tissue on the pre-contrast scan, for each patient, respectively. Embodiments thus place members of the set of images into the same relative intensity range, which is tied to biological meaning associated with the intensity of the stroma or other non-tumor tissue without contrast.

In one embodiment, following pixel-level normalization, image values for each patient are rescaled as integer values from 0 to 255 based on distribution of post-contrast intra-tumoral intensity across the set of images. In this embodiment, the pre-contrast phase and first post-contrast phase are combined into separate channels of a single image, since it is during this initial phase of imaging that the tumor is best distinguished from surrounding tissue due to the effect of enhanced permeability and retention. In another embodiment, image values for each patient may be rescaled as integer values of another, different range. Embodiments may provide as input to the CNN the post-contrast image, or a combination of images from different phases (e.g., pre-contrast, first post-contrast, later post-contrast phases) of the DCE-MRI scan.

In this embodiment, the tumoral region represented in each member of the set of images has been segmented prior to pre-processing. For example, the tumoral region in this embodiment has been automatically segmented by thresholding semi-quantitative pharmacokinetic parameters, including, for example, peak enhancement, and signal enhancement ratio. In another embodiment, the tumoral region may be segmented using other segmentation approaches. For example, the tumoral region may be segmented by a human radiologist. In another example, embodiments may receive un-segmented imagery, and automatically segment the tumoral region using thresholding techniques, or other automated segmentation techniques. FIG. 1 illustrates, at 110, a segmented tumoral region.

Embodiments extract patches from the imagery. FIG. 1 illustrates at 120, patches extracted from the segmented tumor region. In this example, patches with dimensions of 65 pixels by 65 pixels are centered around randomly selected pixels within the tumoral region represented in the slice having the largest tumoral region area, and the two slices adjacent to the slice having the largest tumoral region area. Since, in this example, the number of patients who experienced pCR is smaller than the number of patients who did not, (as indicated in FIG. 2, table 200), tumors from patients responding to treatment may be hyper-sampled to balance out the training data. Thus, in this example, a total of approximately 325000 patches are extracted from the set of images.

Embodiments may train a machine learning classifier using the set of patches. FIG. 1 illustrates, at 130, training a model using the extracted patches. In a preferred embodiment, a CNN is trained using the extracted patches. In this example, a patch size of 65 pixels by 65 pixels is described. Embodiments may employ a CNN having six convolutional blocks, where each convolutional operation decreases the size of the input image (i.e., patch). For example, in one embodiment, the first layer of the CNN includes convolution with a filter size of 3×3, which reduces the dimensions of the input from 65 pixels by 65 pixels to 63 pixels by 63 pixels. In this embodiment, after passing through all the layers of the CNN, the dimensions of the 65 pixel by 65 pixel input image are decreased by 64 pixels. Thus, for an input of a 65 pixel by 65 pixel patch, the output is a single pixel with a value bounded between 0 and 1. This value corresponds to the estimated probability of a patient achieving response, which may be directly compared to a binary response variable in order to train the model. In another embodiment, the CNN may be configured with other, different architectures, including different numbers of layers.

While a patch size of 65 pixels by 65 pixels is described, embodiments may employ other, different patch sizes. For example, in one embodiment, a patch having dimensions larger than 65 pixels by 65 pixels may be input, and the CNN architecture may be adjusted such that the different patch size input is reduced to a single pixel. In another embodiment, a patch having dimensions larger than 65 pixels by 65 pixels may be input, and the CNN architecture may be kept as described herein, thus producing an output that is larger than one pixel. Embodiments may adjust patch size based on a desired training time, a desired predictive accuracy, or desired execution time.

Embodiments may test a machine learning classifier using patches from imagery held out from the data used to train the machine learning classifier. FIG. 1 illustrates, at 140, testing the model trained at 130, using a held-out set of the extracted patches. In one embodiment, the CNN is trained using the extracted patches. In one embodiment, for the testing set, patches are extracted centered around each pixel within the tumoral region. In another embodiment, fewer than all the pixels within the tumoral region may be used. For example, in one embodiment, patches may be generated based on pixels spaced by a fixed amount (i.e., every other pixel), or may be generated from randomly selected pixels. For non-sampled pixels, embodiments may interpolate between predictions to produce a probability mask or heatmap. In one embodiment, a plurality of patches sufficient to cover the tumor region in a non-overlapping manner may be generated. Thus, in one example, for a 130 pixel by 130 pixel tumoral region, four 65 pixel by 65 pixel patches may be extracted.

While FIG. 1 illustrates an exemplary workflow for training and testing a CNN to predict pCR based on pre-NAC therapy DCE-MRI imagery, embodiments may be used to predict pCR in a patient using pre-NAC therapy DCE-MRI imagery. For example, embodiments may be employed to, for a patient, predict post-NAC pCR using pre-NAC DCE-MRI imagery of the patient and a CNN trained as described herein. Embodiments predict pCR from pre-treatment DCR-MRI imagery with an AUC of at least 0.70 and an accuracy of at least 73%. Embodiments are not limited to predicting pCR, but may predict response or non-response.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 5:
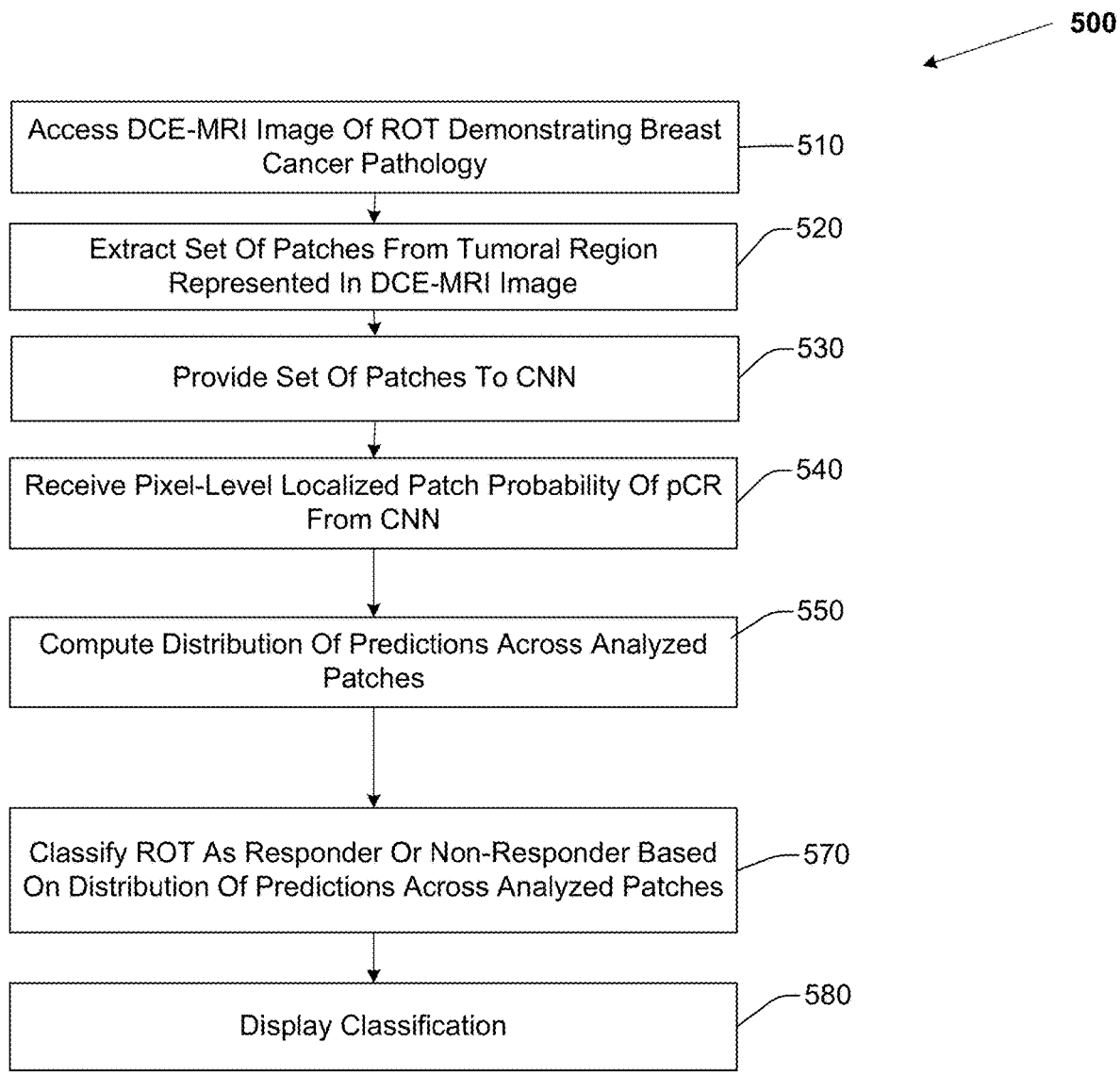
FIG. 5 illustrates operations for predicting pCR from DCE-MRI imagery with a CNN.

FIG. 5 is a flow diagram of example operations 500 that may be performed by a processor to predict response, including, for example, pCR, to NAC in a patient demonstrating breast cancer. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 500 includes, at 510, accessing a pre-NAC radiological image of a region of tissue (ROT) demonstrating breast cancer pathology. The region of tissue includes a tumoral region. The image has a plurality of pixels, a pixel having an intensity. In one embodiment, the pre-NAC radiological image is a pre-NAC dynamic contrast enhanced magnetic resonance imaging (DCE-MRI) image of the region of tissue. The pre-NAC DCE-MRI image is acquired using a 1.5 T magnet, and a four-channel MRI coil or eight-channel MRI coil. In another embodiment, other magnet strengths or numbers of channels may be used to acquire the DCE-MRI image. In one embodiment, the pre-NAC DCE-MRI image has dimensions of 512 pixels by 512 pixels. In another embodiment, the pre-NAC DCE-MRI image may have other, different imaging parameters, including different dimensions. While 512 pixel by 512 pixel DCE-MRI images acquired using a 1.5 T or 3 T magnet and a four-channel MRI coil or eight-channel MRI coil are described in this example, images having other imaging parameters may be employed. Accessing the pre-NAC radiological image includes acquiring electronic data, reading from a computer file, receiving a computer file, reading from a computer memory, or other computerized activity not practically performed in a human mind.

The set of operations 500 also includes, at 520, extracting a set of patches from the tumoral region represented in the pre-NAC radiological image. In one embodiment, the set of patches includes, for each pixel of the tumoral region respectively, a patch centered around the pixel. Embodiments may select patches centered around fewer than all the pixels in the tumoral region. Thus, in another embodiment, the set of patches includes, for a threshold number of pixels that is smaller than the total number of the pixels in the tumoral region, a patch centered around a member of the threshold number of pixels. In one embodiment, a member of the threshold number of pixels is selected based on a pCR predictability level of the pixel, where a pixel having a higher pCR predictability level is more likely to be selected than a pixel having a lower pCR predictability level. In another embodiment, the threshold number of pixels may be user defined, may be defined based on desired performance levels, or may be defined based on available computational resources. In another embodiment, a member of the threshold number of pixels is selected based on a selection pattern. A selection pattern may define, for example, that every other pixel is selected, or that every third pixel is selected.

In one embodiment, a patch has dimensions of 65 pixels by 65 pixels. In another embodiment, a patch may have other, different dimensions. For example, a patch may have dimensions smaller than 65 pixels, or larger than 65 pixels. Patch size may be user selectable. A patch size may be selected based on available computational resources. A patch size may be selected based on properties of the CNN.

For example, a first CNN may be configured to analyze patches of 65 pixels by 65 pixels and output a one-pixel output. A second, different CNN may be configured to analyze patches having larger dimensions (e.g., 100 pixels by 100 pixels), and output a one-pixel output. In yet another embodiment, a third, different CNN may be configured to analyze patches having different dimensions (e.g., 100 pixels by 100 pixels, or 65 pixels by 65 pixels) and to output different sized outputs.

The set of operations 500 also includes, at 530, providing the set of patches to a CNN. The CNN is configured to discriminate tissue that will experience response, including but not limited to pCR, post-NAC from tissue that will not experience response, including but not limited to pCR, post-NAC. In one embodiment, the CNN is a six block CNN. In this embodiment, a block has a convolution layer batch normalization and an activation function. In this embodiment, Blocks 1-5 utilize a rectified linear unit (ReLU) activation function. The final convolutional block of the CNN employs a softmax function to compute the localized patch probability by constraining it to a value between 0 and 1. In this embodiment, the CNN is trained to improve its predictions by minimizing a multinomial logistic objective loss function, a metric computing the distance between the network's predicted probability of response and a patient's binary response outcome (e.g., 0 for non-pCR, 1 for pCR). Incorrect predictions have a higher loss value, and thus information from these examples are weighted more heavily in adjusting the network towards an optimal solution. In another embodiment, the CNN may have another, different architecture. For example, in another embodiment, the CNN may have a different number of blocks or layers, or may employ other functions.

The set of operations 500 also includes, at 540, receiving, from the CNN, a pixel-level localized patch probability of pCR. The CNN computes the pixel-level localized patch probability based, at least in part, on the set of patches. In one embodiment, the CNN is configured to accept a 65 pixel by 65 pixel patch as input, and to output a one-pixel output.

Figure 3:
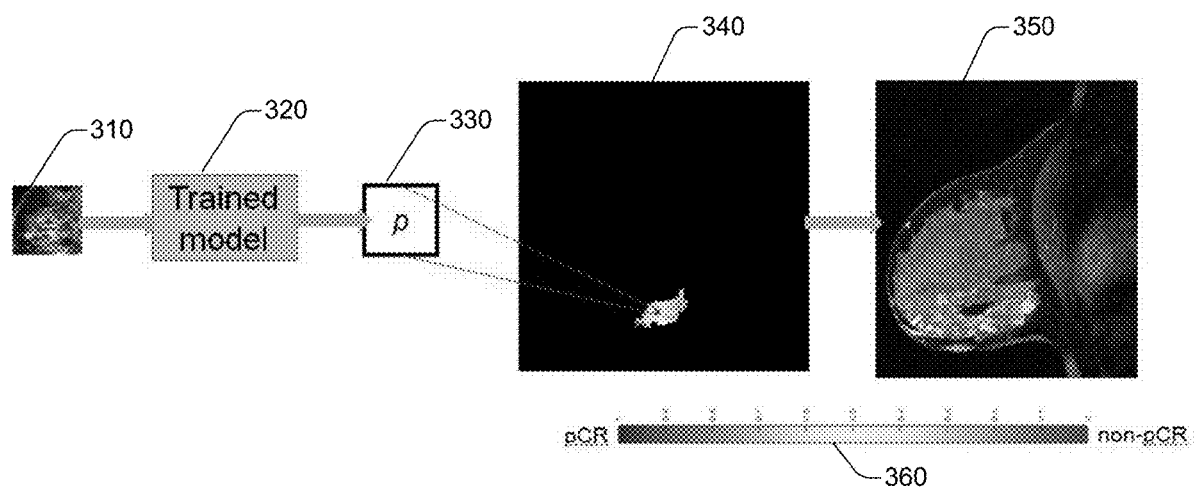
FIG. 3 illustrates an example workflow for generating a heatmap that represents likelihood of pCR in a region of tissue demonstrating BCa.

The set of operations 500 also includes, at 550, computing a distribution of predictions across analyzed patches. The distribution of predictions across analyzed patches is computed based on the pixel-level localized patch probability of pCR. Computing the distribution of prediction across analyzed patches may, in one embodiment, include generating a probability mask based on the pixel-level localized patch probability. FIG. 3 illustrates one example of generating a probability mask. A DCE-MRI image 310 of a region of tissue demonstrating BCa is accessed, the region of tissue including a tumoral region. A set of patches is extracted as described herein, and provided, at 320, to a CNN trained as described herein. The CNN outputs, at 330, a pixel-level localized patch probability of pCR. For each pixel in the tumoral region, a probability mask is generated at 340.

The set of operations 500 also includes, at 570, classifying the region of tissue as a responder or non-responder based, at least in part, on the distribution of predictions across analyzed patches. In one embodiment, classifying the region of tissue as a responder or non-responder based, at least in part, on the distribution of predictions across analyzed patches, includes classifying the region of tissue using a majority voting scheme. In this embodiment, upon determining that at least 50% of the pixels in the distribution of predictions across analyzed patches are more likely to experience pCR than not, the region of tissue is classified as a responder. In another embodiment, other classification schemes may be employed. For example, the region of tissue may be classified as a responder when at least 60% of the pixels in the distribution of predictions across analyzed patches are more likely to experience pCR than not.

The set of operations 500 further includes, at 580, displaying the classification. Displaying the classification may, in one embodiment, further include displaying the distribution of predictions across analyzed patches. Displaying the distribution of predictions across analyzed patches or the classification may include displaying the distribution of predictions across analyzed patches or the classification on a computer monitor, a smartphone display, a tablet display, or other displays. Displaying the distribution of predictions across analyzed patches and the classification may also include printing the distribution of predictions across analyzed patches and the classification. Displaying the distribution of predictions across analyzed patches and the classification may also include controlling a pCR prediction system, a personalized medicine system, a monitor, or other display, to display operating parameters or characteristics of a machine learning classifier, during both training and testing, or during clinical operation of the machine learning classifier. By displaying the distribution of predictions across analyzed patches and the classification, example embodiments provide a timely and intuitive way for a human medical practitioner to more accurately classify a region of tissue represented in DCE-MRI images as likely to respond, including but not limited to pCR, or unlikely to respond, including but not limited to pCR, thus improving on existing approaches to predicting response, including pCR, that rely non-purpose built CNNs or other machine learning techniques. Embodiments may further display the radiological image, including the pre-contrast image or the post-contrast image. Embodiments may further display operating parameters of the CNN. Embodiments may further display a member of the set of patches, or the probability mask.

Figure 11:
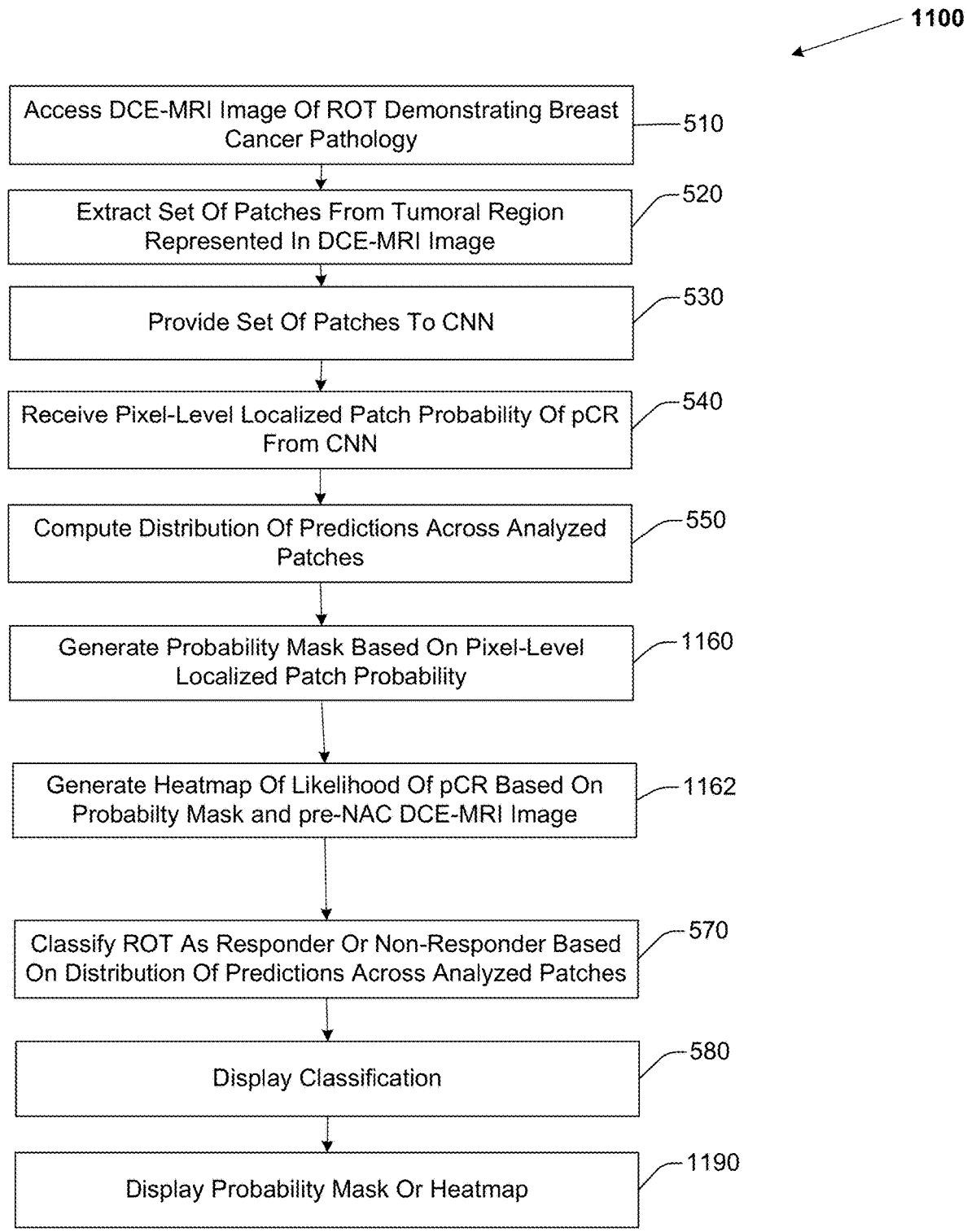
FIG. 11 illustrates operations for predicting pCR from DCE-MRI imagery with a CNN.

FIG. 11 illustrates a set of operations 1100 that is similar to operations 500 but that includes additional details and steps. The set of operations includes, at 1160, generating a probability mask based on the pixel-level localized patch probability. The set of operations 1100 also includes, at 1162, generating a heatmap of likelihood of response to NAC. The heatmap is generated based on the probability mask and the pre-NAC radiological image. FIG. 3 further illustrates an exemplary heatmap 350, that includes the initial DCR-MRI image 310 (enlarged in FIG. 3 for ease of viewing), overlaid with the probability mask illustrated at 340. A legend 360 is also illustrated. The set of operations 1100 further includes, at 1190, displaying the probability mask or heatmap. While embodiments describe generating and displaying a probability mask, and generating and displaying a heatmap based on the probability mask, other techniques for displaying the likelihoods or probabilities of response, including but not limited to pCR, at every voxel in the image, or at a threshold number of voxels, may be employed.

In one embodiment, the operations 500 further include training the CNN classifier as described herein. The CNN may be trained using a set of training images acquired from a plurality of MRI scans of different patients. A member of the set of training images may be a DCE-MRI image of a region of tissue demonstrating BCa, where at least one member of the set of training images is of a region of tissue acquired of a patient that responded to chemotherapy, including experiencing pCR, and at least one other, different member of the set of training images is of a region of tissue acquired of a patient that did not respond to chemotherapy (e.g., did not experience pCR). While response, including pCR is a patient-wise label, in embodiments described herein, when training the CNN, a patch from a patient that experienced pCR is labeled, for example, as a "1", and a patch from a patient that did not experience pCR is labeled, for example, as a "0". In training, the CNN does not receive localization information with respect to individual patches. A member of the set of training images has a plurality of pixels, a pixel having an intensity. The set of images or patches used for network training may be expanded by applying alterations, such as rotation and mirroring, to the original patches to improve network performance and generalizability. Training the machine learning classifier may include training the machine learning classifier until a threshold level of accuracy or loss is achieved, until a threshold time has been spent training the machine learning classifier, until a number of iterations updating the CNN with the full set of patches (known as an "epoch"), until a threshold amount of computational resources have been expended training the machine learning classifier, until a user terminates training, or some combination thereof. Other training termination conditions may be employed. Training the machine learning classifier may also include determining which patch size, or number of patches, or region of a tumoral region, is most discriminative in distinguishing a positive class from a negative class (e.g., responder vs non-responder, pCR vs non-pCR), as well as determining settings outside the CNN architecture but relevant to its learning behavior (e.g. learning rate, the number of patches used to update the network at a single time, use of dropout and regularization).

While FIG. 5 illustrates various actions occurring in serial, it is to be appreciated that various actions illustrated in FIG. 5 could occur substantially in parallel. By way of illustration, a first process could involve accessing a DCE-MRI image, a second process could involve extracting patches from a tumor region represented in the DCE-MRI image, and a third process could involve providing a patch to a CNN. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 500 or 600 or 1100, methods 1000 or 1200, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved prediction of response, including pCR, may produce the technical effect of improving the administration of NAC, by increasing the accuracy of and decreasing the time required to determine if a patient is likely or unlikely to experience pCR post-NAC. Treatments and resources, including expensive chemotherapy agents may be more accurately tailored to patients with a likelihood of benefiting from said treatments and resources, including responding to chemotherapy, so that more appropriate treatment protocols may be employed, and expensive resources are not wasted, when DCE-MRI images are more accurately and more quickly assessed for likelihood of pCR. Controlling a pCR prediction apparatus based on improved, more accurate analysis of DCE-MRI images further improves the operation of the system, processor, or apparatus, since the accuracy of the system, processor, or apparatus is increased and unnecessary operations will not be performed. Embodiments described herein, including at least operations 500, 600, and 1100, apparatus 700 and 800, or methods 1000, and 1200, resolve features extracted from DCE-MRI imagery at a higher order or higher level than a human can resolve in the human mind or with pencil and paper. For example, properties of the DCE-MRI image that are not perceivable by the human eye may be detected by embodiments. Pixel-wise probabilities and heatmaps generated by embodiments are not properties of tumoral tissue that are perceivable by the human eye, and their computation is not practically performed in the human mind. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Figure 6:
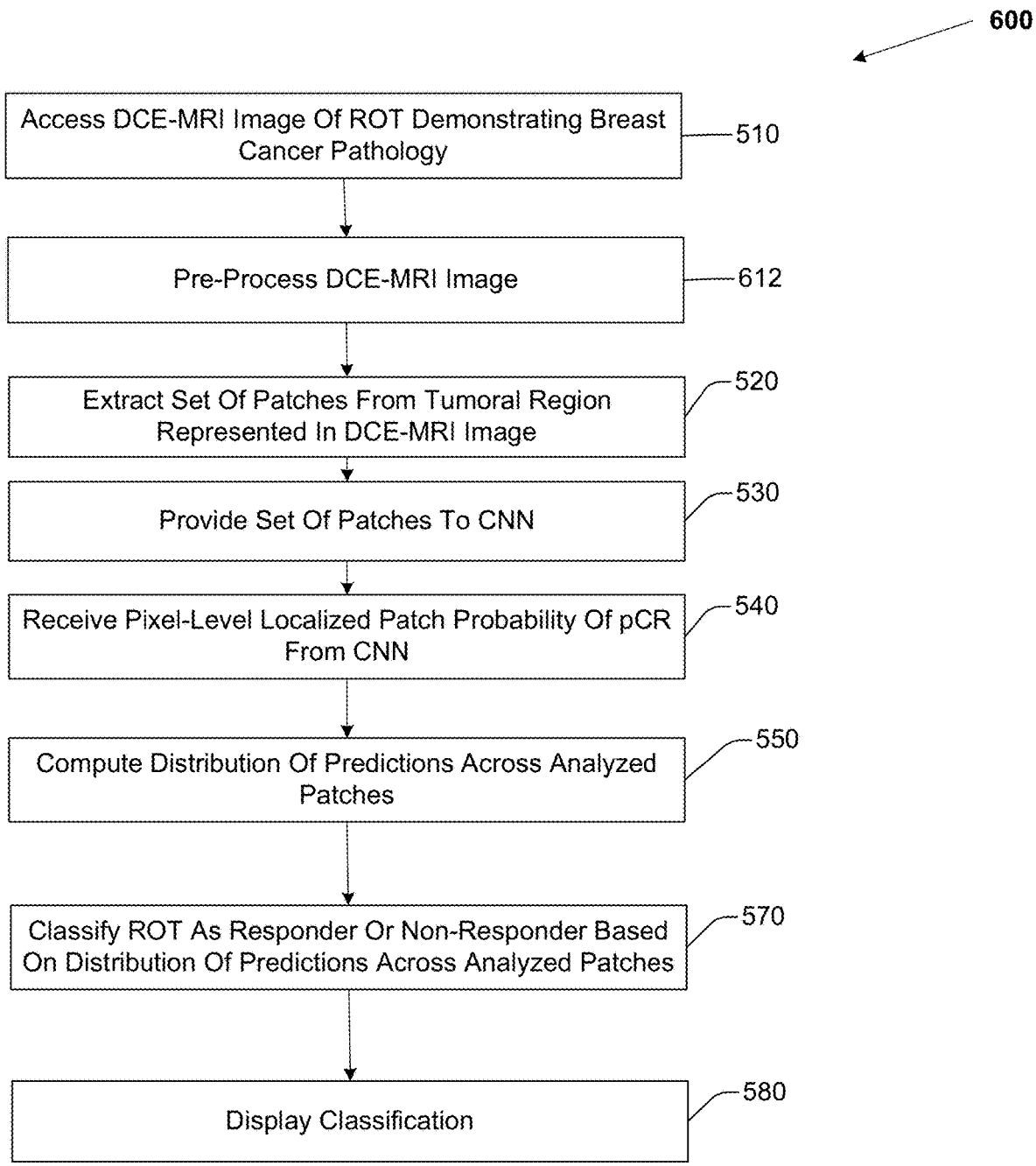
FIG. 6 illustrates operations for predicting pCR from DCE-MRI imagery with a CNN.

FIG. 6 illustrates a set of operations 600 that is similar to operations 500 but that includes additional details and elements. The set of operations 600 includes, at 612, pre-processing the pre-NAC radiological image. In this embodiment, accessing the pre-NAC radiological image includes accessing a set of pre-NAC DCE-MRI images of the region of tissue. The set of pre-NAC DCE-MRI images including a pre-contrast image and a post-contrast image. In this embodiment, a member of the set of pre-NAC DCE-MRI images is acquired using a 1.5 T magnet and a four-channel MRI coil or eight-channel MRI coil. In this embodiment, a member of the set of pre-NAC DCE-MRI images has dimensions of 512 pixels by 512 pixels. In this embodiment, pre-processing the pre-NAC radiological image includes generating a pre-processed image by normalizing the post-contrast image to the mean intensity of a reference region of the pre-contrast image as described herein. The reference region includes a stroma or other non-tumor region represented in the pre-contrast image. In this embodiment, extracting the set of patches from the tumoral region comprises extracting a set of patches from the tumoral region represented in the pre-processed image.

In one embodiment, generating the pre-processed image may further include standardizing images to a fixed range of intensity values based on distribution across a collection of imaging data from multiple patients. Embodiment may rescale image values for a patient as integer values from 0 to 255 based on distribution of post-contrast intra-tumoral intensity across the set of images. In this embodiment, the pre-contrast phase and first post-contrast phase are combined into separate channels of a single image. In another embodiment, image values for a patient may be rescaled as integer values of another, different range.

Figure 7:
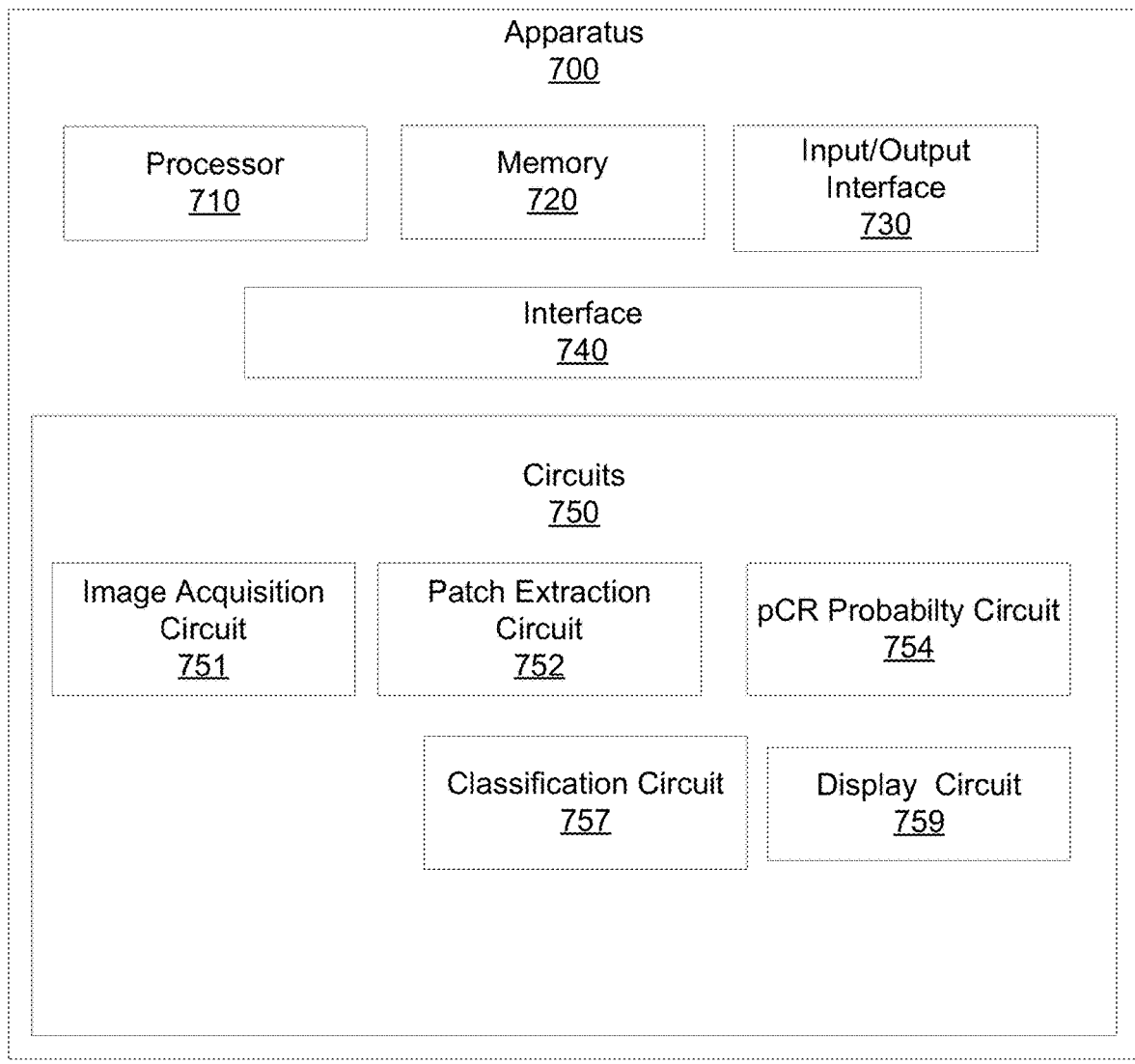
FIG. 7 illustrates an example apparatus for predicting pCR from DCE-MRI imagery.

FIG. 7 illustrates an example apparatus 700. Apparatus 700 may be configured to predict response, including pCR, in breast cancer. Apparatus 700 includes a processor 710. Apparatus 700 also includes a memory 720. Processor 710 may, in one embodiment, include circuitry such as, but not limited to, one or more single-core or multi-core processors. Processor 710 may include any combination of general-purpose processors and dedicated processors (e.g., graphics processors, application processors, etc.). The processors may be coupled with or may include memory (e.g. memory 720) or storage and may be configured to execute instructions stored in the memory 720 or storage to enable various apparatus, applications, or operating systems to perform the operations. Memory 720 is configured to store a radiological image of a region of tissue demonstrating breast cancer. The radiological image has a plurality of pixels, a pixel having an intensity. Memory 720 may be further configured to store a training set of radiological images, or a testing set of radiological images.

Apparatus 700 also includes an input/output (I/O) interface 730, a set of circuits 750, and an interface 740 that connects the processor 710, the memory 720, the I/O interface 730, and the set of circuits 750. I/O interface 730 may be configured to transfer data between memory 720, processor 710, circuits 750, and external devices, for example, an MRI system or a pCR prediction system.

The set of circuits 750 includes an image acquisition circuit 751, a patch extraction circuit 752, a pCR probability circuit 754, a classification circuit 757, and a display circuit 759. The image acquisition circuit 751 is configured to access a radiological image of a region of tissue demonstrating breast cancer. The radiological image has a plurality of pixels, a pixel having an intensity. In one embodiment the radiological image is a pre-NAC radiological image of a region of tissue demonstrating BCa pathology. In another embodiment, other types of image may be accessed or employed. Accessing the radiological image may include accessing a radiological image stored in memory 720. In one embodiment, accessing the radiological image may include accessing a radiological image stored in a data storage device, including a hard disk drive, a solid state device, a tape drive, or accessing a radiological image over a local area network. Accessing the radiological image includes acquiring electronic data, reading from a computer file, receiving a computer file, reading from a computer memory, or other computerized activity not practically performed in the human mind.

Patch extraction circuit 752 is configured to extract a set of patches from the tumoral region. In one embodiment patch extraction circuit 752 is configured to, for each pixel in the tumoral region represented in the radiological image, extract a patch centered on each pixel, respectively. In another embodiment patch extraction circuit 752 is configured to, for a threshold number of pixels in the tumoral region, extract a patch centered on each of the threshold number of pixels, respectively. In this embodiment, the threshold number of pixels is less than the number of pixels in the tumoral region. In one embodiment, a member of the threshold number of pixels is selected based on a pCR predictability level of the pixel. In another embodiment, a member of the threshold number of pixels is selected based on a different condition. For example, in one embodiment, every other pixel may be selected for patch generation. In another embodiment, pixels may be selected based on a patch size, such that the set of patches covers the entire tumoral region without overlap.

pCR probability circuit 754 is configured to compute a pixel-level pCR probability that the region of tissue will experience pCR post-NAC. pCR probability circuit 754 computes the probability based, at least in part, on the set of patches. In one embodiment, pCR probability circuit 754 is configured as a CNN, or includes circuitry configured as a CNN, the CNN having six blocks. In this embodiment, a block has a convolution layer having batch normalization and a ReLU. Also in this embodiment, the CNN employs a multinomial logistic objective loss function for optimization. In this embodiment, the CNN computes the pixel-level pCR probability using a softmax function. In another embodiment, other functions may be employed for optimization or for computing the final pixel-level probability. In another embodiment, the CNN may have another, different number of blocks or layers. While in this embodiment, pCR probability circuit 754 is configured to compute a pixel-level probability that the region of tissue will experience pCR, embodiments are not limited to predicting pCR, but may predict response to chemotherapy.

Classification circuit 757 is configured to generate a classification of the region of tissue as a responder or non-responder (e.g., likely to experience pCR, unlikely to experience pCR) based, at least in part, on the pixel-level pCR probability. In one embodiment, classification circuit 757 is configured to generate the classification using a majority voting scheme. In another embodiment, classification circuit 757 may be configured to generate the classification using another, different scheme.

Display circuit 759 is configured to display the pixel-level pCR probability and the classification. In one embodiment, display circuit 759 is further configured to display at least one of the radiological image, the set of patches, or a member of the set of patches. Displaying the pixel-level pCR probability and the classification, or at least one of the radiological image, the set of patches, or a member of the set of patches may also include printing the pixel-level pCR probability, the classification, or at least one of the radiological image, the set of patches, or a member of the set of patches.

Figure 8:
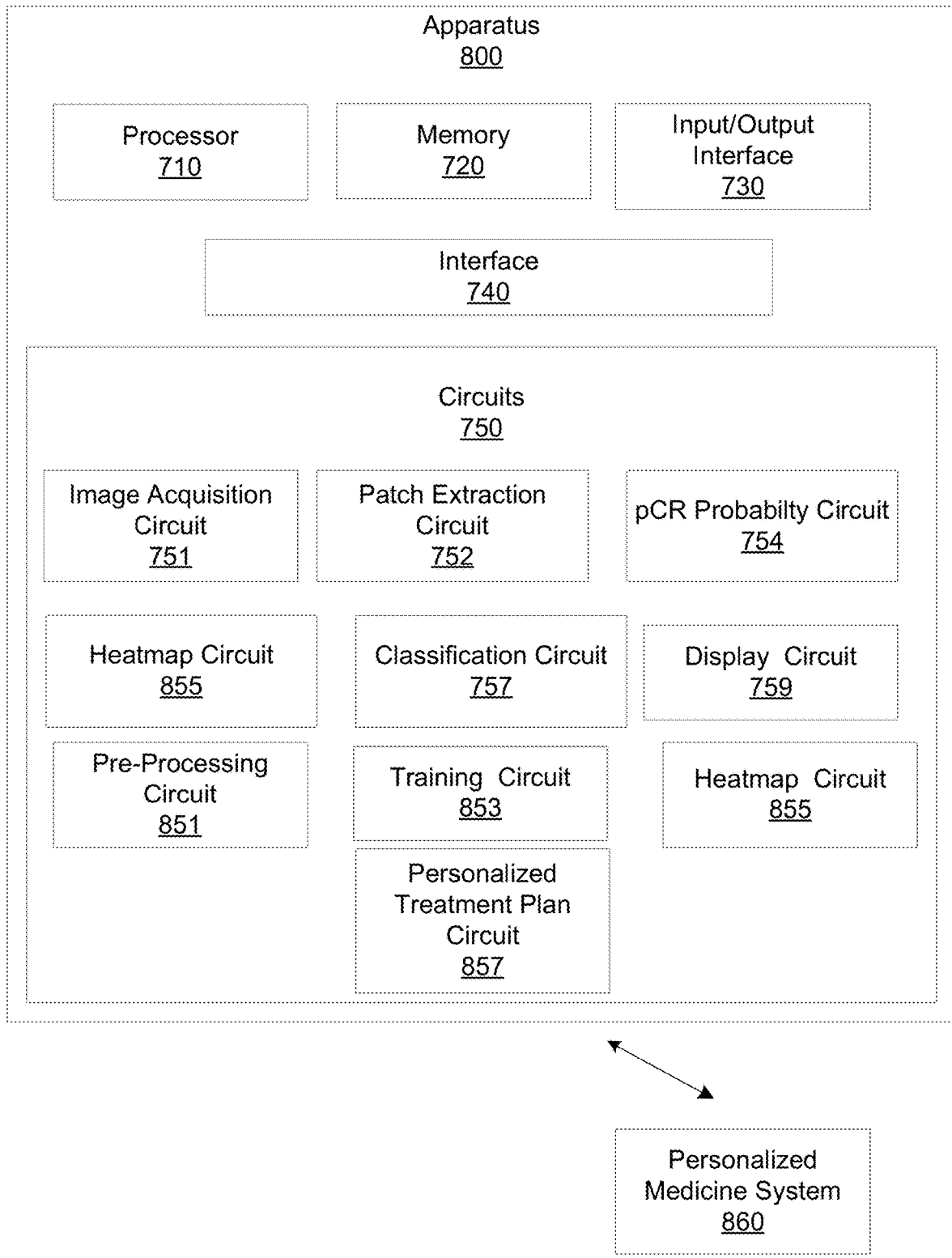
FIG. 8 illustrates an example apparatus for predicting pCR from DCE-MRI imagery.

FIG. 8 illustrates an example apparatus 800 that is similar to apparatus 700 but that includes additional details and elements. In one embodiment, apparatus 800 includes a training circuit 853. The training circuit 853 may be configured to train pCR probability circuit 754, a machine learning classifier, including a CNN, to classify a region of tissue demonstrating BCa according to techniques described herein. In one embodiment, training circuit 853 is configured to access a training dataset of radiological images of tissue demonstrating breast cancer, where a first subset of the training dataset includes tissue that experienced pCR post-NAC, and a second, disjoint subset of training dataset includes tissue that did not experience pCR post-NAC. The training circuit 853 may be further configured to access a testing dataset of radiological images of tissue demonstrating breast cancer, where a first subset of the testing dataset includes tissue that experienced pCR post-NAC, and a second, disjoint subset of testing dataset includes tissue that did not experience pCR post-NAC. In this embodiment, the machine learning classifier is trained and tested using the training dataset of radiological images and the testing dataset of radiological images. Training the machine learning classifier may include training the machine learning classifier until a threshold level of accuracy or loss is achieved, until a threshold time has been spent training the machine learning classifier, until a number of iterations updating the CNN with the full set of patches (known as an "epoch"), until a threshold amount of computational resources have been expended training the machine learning classifier, until a user terminates training, or some combination thereof. Other training termination conditions may be employed. Once a network (i.e., CNN) has been trained, it can be applied to new imaging data without repeating training, however training may optionally be repeated in order to make adjustments to a network given a new set of training data, for example to improve performance among images acquired with a different type of MRI scanner or at a new medical institution.

Apparatus 800 also includes heatmap circuit 855. Heatmap circuit 855 is configured to generate a pixel-wise probability mask based on the pixel-level pCR probability. Heatmap circuit 855 is further configured to generate a heatmap of likelihood of response to NAC based, at least in part, on the pixel-wise probability mask and the pre-NAC radiological image. In this embodiment, display circuit 759 is further configured to display at least one of the heatmap or the pixel-wise probability mask.

Apparatus 800 also includes pre-processing circuit 851. In this embodiment, image acquisition circuit 751 is further configured to access a second pre-NAC radiological image of the region of tissue, where the second pre-NAC radiological image is a pre-contrast DCE-MRI image. In this embodiment, pre-processing circuit 851 is configured to normalize the pre-NAC radiological image by normalizing the intensity of a pixel in the pre-NAC radiological image to the mean intensity of a reference region of the second pre-NAC radiological image. The reference region includes a stroma region or other non-tumor region represented in the second pre-NAC radiological image (i.e., in the pre-contrast image). Pre-processing circuit 851 may be further configured to standardize images to a fixed range of intensity values based on distribution across a collection of imaging data from multiple patients.

Pre-processing circuit 851 may be further configured to rescale image values for a patient as integer values from 0 to 255 based on distribution of post-contrast intra-tumoral intensity across the set of images. In this embodiment, the pre-contrast phase and first post-contrast phase are combined into separate channels of a single image. In another embodiment, pre-processing circuit 851 may be configured to rescale image values for a patient as integer values of another, different range.

Apparatus 800 also includes personalized treatment plan circuit 857. Personalized treatment plan circuit 857 is configured to generate a personalized BCa treatment plan based, at least in part, on the classification. The personalized treatment plan circuit 857 may be further configured to generate the personalized BCa treatment plan based the pixel-wise probability map or the heatmap. Personalized treatment plan circuit 857 may be configured to generate a personalized BCa treatment plan for the patient of whom the radiological image was acquired based, at least in part, on the classification, the radiological image, the pixel-wise probability map or, or the heatmap. Defining a personalized BCa treatment plan facilitates delivering a particular treatment that will be therapeutically active to the patient, while minimizing negative or adverse effects experienced by the patient. For example, the personalized BCa treatment plan may suggest a surgical treatment, may define an immunotherapy agent dosage or schedule, or a chemotherapy agent dosage or schedule, for a patient identified as likely to experience pCR. For a patient classified as unlikely to achieve pCR, other treatments may be suggested.

FIG. 8 further illustrates personalized medicine device 860. Apparatus 800 may be configured to provide the classification, the pixel-wise probability map, the heatmap, or other data to personalized medicine device 860. Personalized medicine device 860 may be, for example, a CADx system, a BCa pCR prediction system, or other type of personalized medicine device that may be used to facilitate the prediction of patient response. In one embodiment, personalized treatment plan circuit 855 may control personalized medicine device 860 to display the personalized BCa treatment plan, the classification, the heatmap, the radiological image, or a member of the set of patches on a computer monitor, a smartphone display, a tablet display, or other displays.

Figure 9:
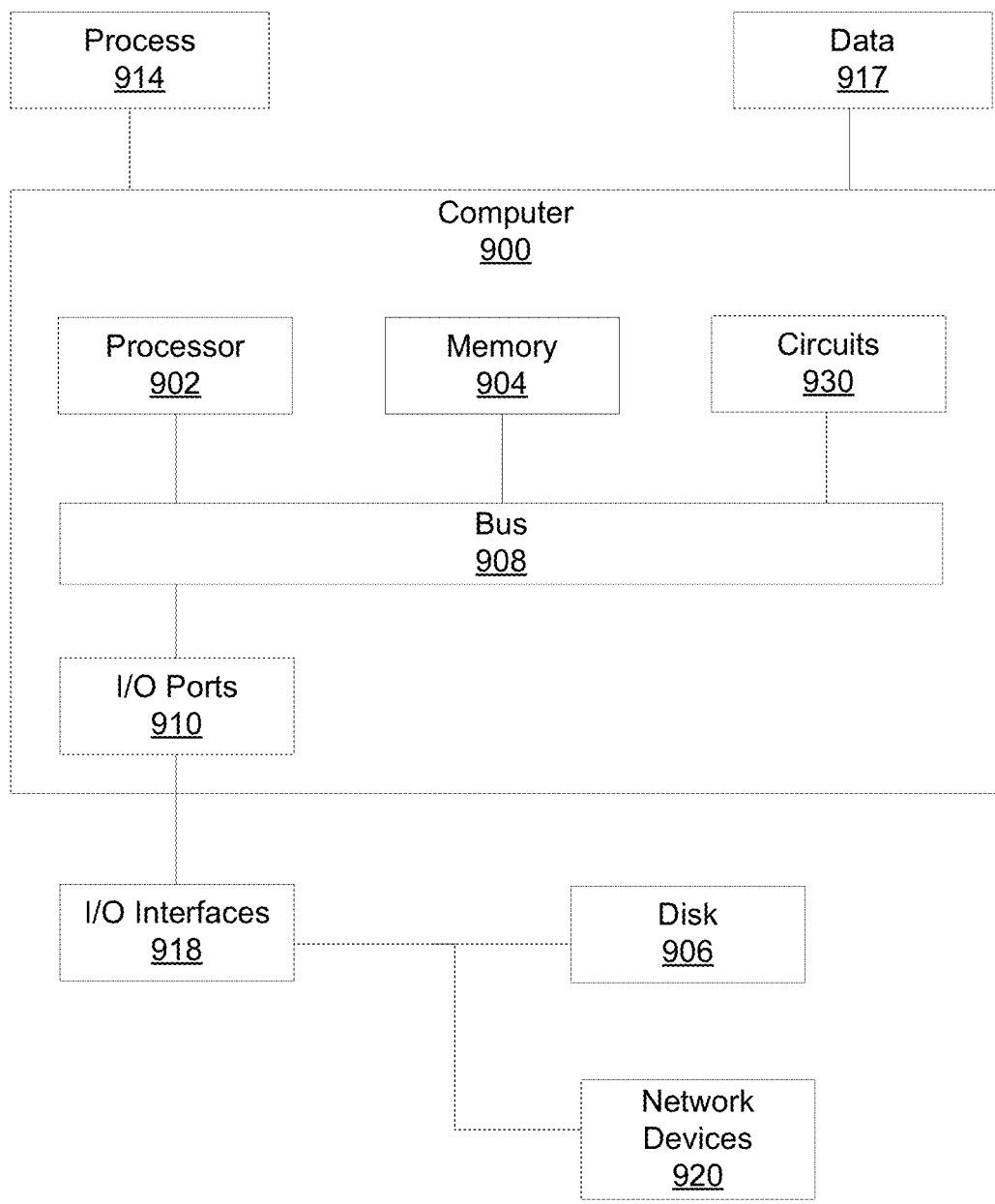
FIG. 9 illustrates an example computer in which embodiments described herein may operate.

FIG. 9 illustrates an example computer 900 in which example methods illustrated herein can operate and in which example methods, apparatus, circuits, operations, or logics may be implemented. In different examples, computer 900 may be part of a pCR prediction system or apparatus, or an MRI system, or may be operably connectable to a pCR prediction system or apparatus, or an MRI system.

Computer 900 includes a processor 902, a memory 904, and input/output (I/O) ports 910 operably connected by a bus 908. In one example, computer 900 may include a set of logics or circuits 930 that perform operations for or a method of predicting response, including pCR, to chemotherapy, using a machine learning classifier. Thus, the set of circuits 930, whether implemented in computer 900 as hardware, firmware, software, and/or a combination thereof may provide means (e.g., hardware, firmware, circuits) for performing pCR prediction based on pre-NAC DCE-MRI imagery of tissue demonstrating breast cancer. In different examples, the set of circuits 930 may be permanently and/or removably attached to computer 900.

Processor 902 can be a variety of various processors including dual microprocessor and other multi-processor architectures. Processor 902 may be configured to perform steps of methods claimed and described herein. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a flash memory card, or a memory stick. Furthermore, disk 906 may include optical drives like a CD-ROM or a digital video ROM drive (DVD ROM). Memory 904 can store processes 914 or data 917, for example. Data 917 may, in one embodiment, include DCE-MRI images. Disk 906 or memory 904 can store an operating system that controls and allocates resources of computer 900.

Bus 908 can be a single internal bus interconnect architecture or other bus or mesh architectures. While a single bus is illustrated, it is to be appreciated that computer 900 may communicate with various devices, circuits, logics, and peripherals using other buses that are not illustrated (e.g., PCIE, SATA, Infiniband, 794, USB, Ethernet).

Computer 900 may interact with input/output devices via I/O interfaces 918 and input/output ports 910. Input/output devices can include, but are not limited to, CT systems, MRI systems, digital whole slide scanners, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks, including the cloud.

Figure 10:
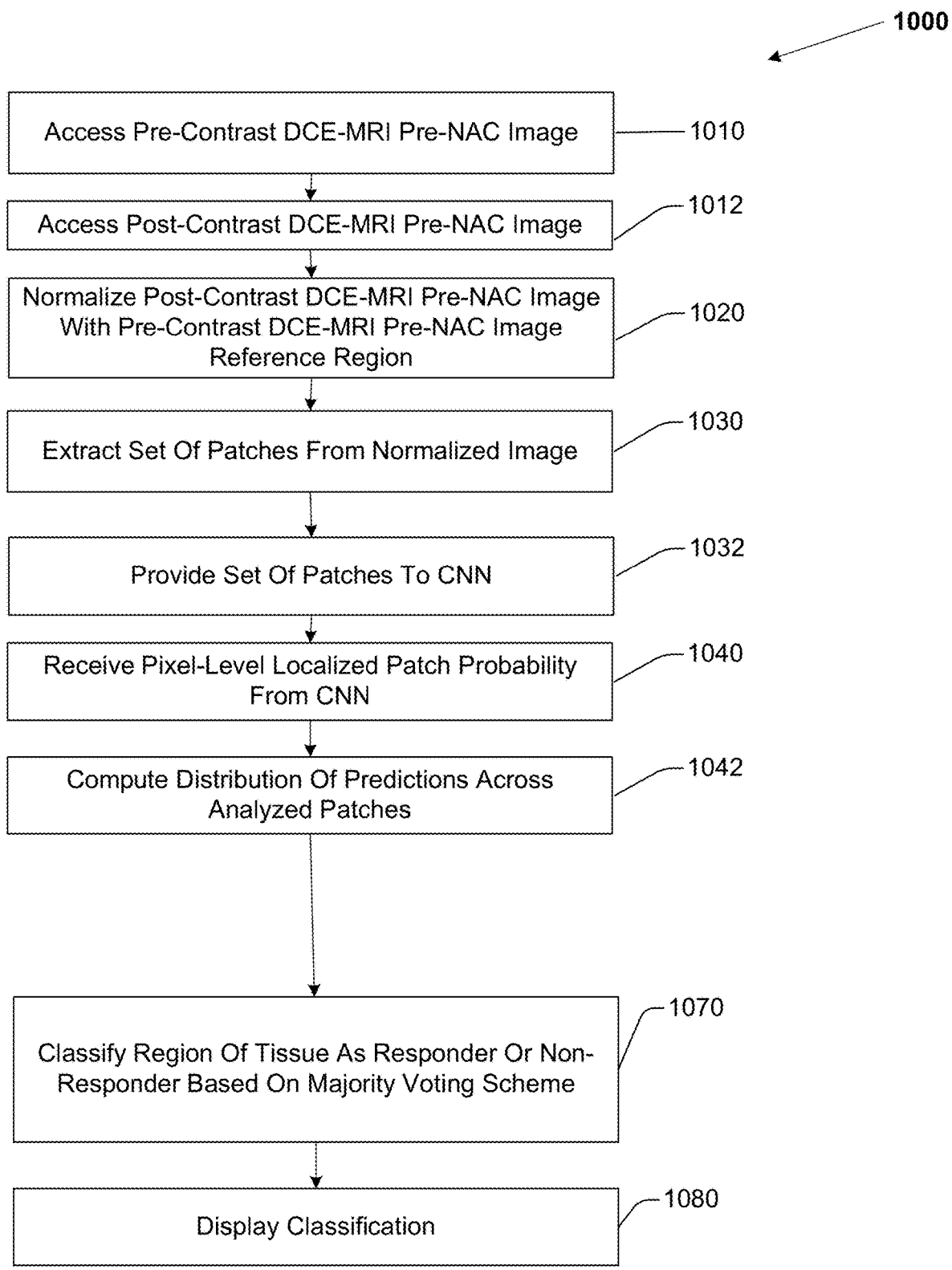
FIG. 10 illustrates an example method for predicting pCR from DCE-MRI imagery with a CNN.

FIG. 10 illustrates an example method 1000. Method 1000 includes, at 1010, accessing a pre-contrast DCE-MRI pre-NAC image of a region of tissue demonstrating BCa pathology. The region of tissue includes a tumoral region. The pre-contrast DCE-MRI image has a plurality of pixels, a pixel having an intensity. Accessing the pre-contrast DCE-MRI image includes acquiring electronic data, reading from a computer file, receiving a computer file, reading from a computer memory, or other computerized activity not practically performed in a human mind.

Method 1000 also includes, at 1012, accessing a post-contrast DCE-MRI pre-NAC image of the region of tissue. The post-contrast DCE-MRI image has a plurality of pixels, a pixel having an intensity. Accessing the post-contrast DCE-MRI image includes acquiring electronic data, reading from a computer file, receiving a computer file, reading from a computer memory, or other computerized activity not practically performed in a human mind.

Method 1000 also includes, at 1020, generating a normalized image by normalizing the post-contrast DCE-MRI image to the mean intensity of a reference region of the pre-contrast DCE-MRI image. The reference region may be located in stroma represented in the pre-contrast DCE-MRI image. Generating the normalized image includes acquiring electronic data, reading from a computer file, receiving a computer file, reading from a computer memory, or other computerized activity not practically performed in a human mind.

Method 1000 also includes, at 1030, extracting a set of patches from the tumoral region represented in the normalized image. A member of the set of patches is centered on a member of a set of pixels, where a member of the set of pixels is selected based on a pCR predictiveness of the member of the set of pixels. In another embodiment, extracting the set of patches includes extracting a patch centered on each pixel of the tumoral region, respectively. Extracting the set of patches includes acquiring electronic data, reading from a computer file, receiving a computer file, reading from a computer memory, or other computerized activity not practically performed in a human mind.

Method 1000 also includes, at 1032, providing the set of patches to a CNN configured to discriminate tissue that will experience pCR post-NAC from tissue that will not experience pCR post-NAC. Providing the set of patches to the CNN includes acquiring electronic data, reading from a computer file, receiving a computer file, reading from a computer memory, or other computerized activity not practically performed in a human mind. The CNN may have, in one embodiment, a six-layer architecture. The CNN may be configured, in this embodiment, to accept an input (e.g., a member of the set of patches) having a first size (e.g., 65 pixels by 65 pixels), and generate an output having a second, different size (e.g., one pixel). In one embodiment, the CNN is configured to discriminate tissue that will experience response post-NAC from tissue that will not experience response post-NAC.

Method 1000 also includes, at 1040, receiving, from the CNN, a pixel-level localized patch probability of pCR. The CNN computes the pixel-level localized patch probability based, at least in part, on the set of patches. Receiving, from the CNN, the pixel-level localized patch probability includes acquiring electronic data, reading from a computer file, receiving a computer file, reading from a computer memory, or other computerized activity not practically performed in a human mind. In one embodiment, method 1000 includes, at 1040, receiving, from the CNN, a pixel-level localized patch probability of response.

Method 1000 also includes, at 1042, computing a distribution of predictions across analyzed patches. The distribution of predictions across analyzed patches is computed based on the pixel-level localized patch probability of pCR. Generating the distribution of predictions across analyzed patches includes acquiring electronic data, reading from a computer file, receiving a computer file, reading from a computer memory, or other computerized activity not practically performed in a human mind.

Method 1000 also includes, at 1070, classifying the region of tissue as a responder or non-responder based, at least in part, on a majority voting scheme. In one embodiment, classifying the region of tissue as a responder or non-responder includes classifying the region of tissue as likely to experience pCR or unlikely to experience pCR. The majority voting scheme may be applied to the distribution of predictions across analyzed patches. Classifying the region of tissue includes acquiring electronic data, reading from a computer file, receiving a computer file, reading from a computer memory, or other computerized activity not practically performed in a human mind.

Method 1000 further includes, at 1080, displaying the classification. Displaying the classification includes acquiring electronic data, reading from a computer file, receiving a computer file, reading from a computer memory, or other computerized activity not practically performed in a human mind. Displaying the classification may further include, in one embodiment, displaying at least one of the pre-contrast DCE-MRI image, the post-contrast DCE-MRI image, the set of patches, the pixel-level localized patch probability, or the distribution of predictions across analyzed patches.

Figure 12:
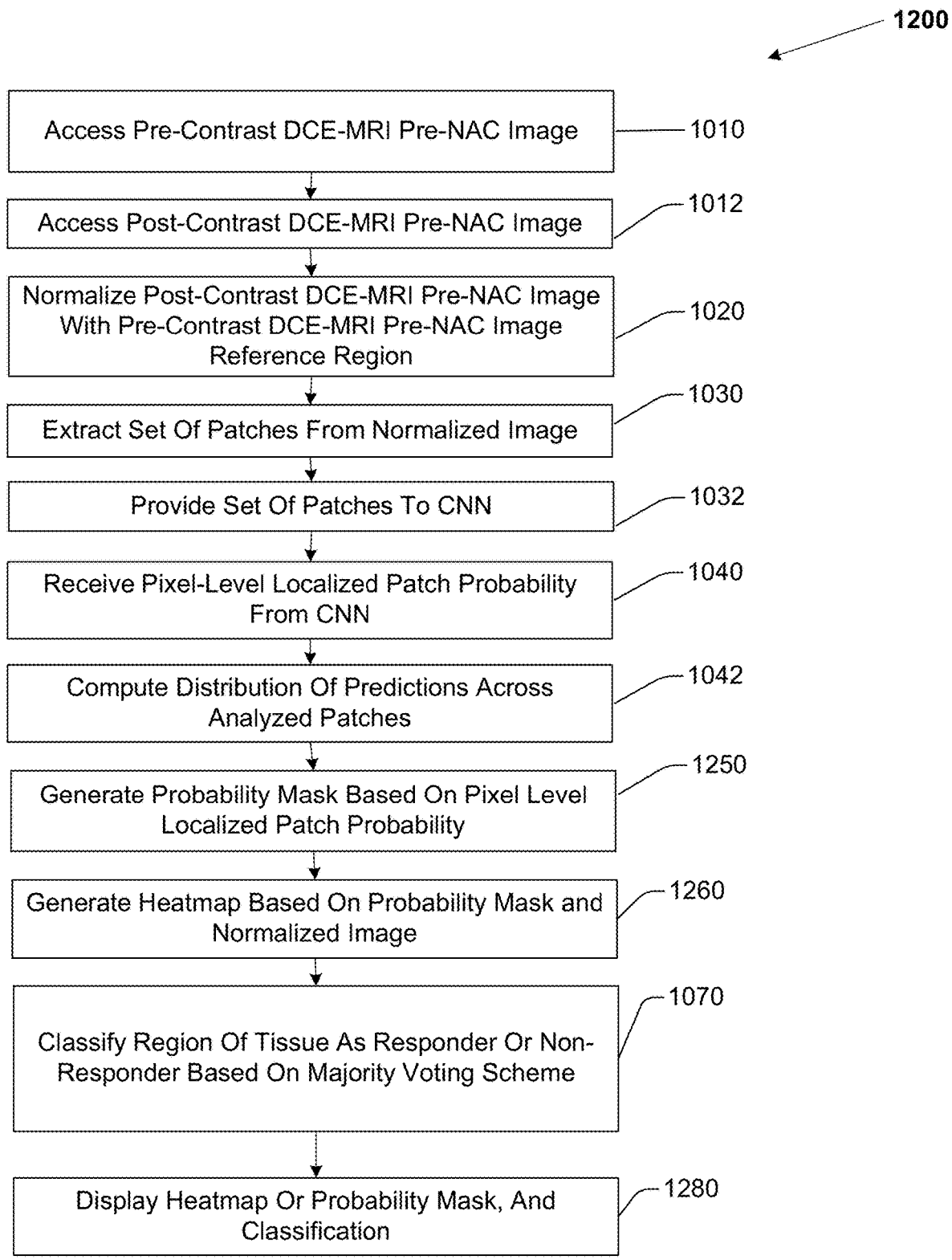
FIG. 12 illustrates an example method for predicting pCR from DCE-MRI imagery with a CNN.

FIG. 12 illustrates a method 1200 that is similar to method 1000 but that includes additional elements and details. In one embodiment, method 1200 includes, at 1250 generating a probability mask of the tumoral region based on the pixel-level localized patch probability.

In one embodiment, method 1200 may further include, at 1260, generating a heatmap of likelihood of response to NAC based on the probability mask and the normalized image. Generating the heatmap or the probability mask includes acquiring electronic data, reading from a computer file, receiving a computer file, reading from a computer memory, or other computerized activity not practically performed in a human mind.

In one embodiment, method 1000 or method 1200 may further display, at 1080 or 1280, the classification, the probability mask, the heatmap, the normalized image, the pre-contrast DCE-MRI image, the post-contrast DCE-MRI image, the distribution of predictions across analyzed patches, or a member of the set of patches.

Examples herein can include subject matter such as an apparatus, a pCR prediction system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting response, including pCR, to NAC, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed control a processor to perform operations, the operations comprising:
    accessing a pre-neoadjuvant chemotherapy (NAC) radiological image of a region of tissue demonstrating breast cancer pathology, the region of tissue including a tumoral region, the image having a plurality of pixels, a pixel having an intensity;
    extracting a set of patches from the tumoral region;
    providing the set of patches to a convolutional neural network (CNN) configured to discriminate tissue that will experience pathological complete response (pCR) post-NAC from tissue that will not experience pCR post-NAC;
    receiving, from the CNN, a pixel-level localized patch probability of pCR, where the CNN computes the pixel-level localized patch probability based, at least in part, on the set of patches;
    computing a distribution of predictions across analyzed patches based on the pixel-level localized patch probability of pCR;
    classifying the region of tissue as a responder or non-responder based, at least in part, on the distribution of predictions across analyzed patches; and
    displaying the classification.

2. The non-transitory computer-readable storage device of claim 1, where accessing the image includes accessing a set of pre-NAC dynamic contrast enhanced magnetic resonance imaging (DCE-MRI) images of the region of tissue, the set of pre-NAC DCE-MRI images including a pre-contrast image and at least one post-contrast image.

3. The non-transitory computer-readable storage device of claim 2, where a member of the set of pre-NAC DCE-MRI images is acquired using a 1.5 T or 3 T magnet and a four-channel MRI coil or eight-channel MRI coil.

4. The non-transitory computer-readable storage device of claim 2, the operations further comprising:
    generating a pre-processed image by:
        normalizing the at least one post-contrast image to the mean intensity of a reference region of the pre-contrast image, the reference region including a stroma region in stroma or other non-tumor reference tissue represented in the pre-contrast image; or
        standardizing images to a fixed range of intensity values based on distribution across a collection of imaging data from multiple patients; and
    where extracting the set of patches from the tumoral region comprises extracting a set of patches from the tumoral region represented in the pre-processed image.

5. The non-transitory computer-readable storage device of claim 1, where the set of patches includes, for each pixel of the image respectively, a patch centered around the pixel.

6. The non-transitory computer-readable storage device of claim 1, where the set of patches includes, for a threshold number of pixels that is smaller than the total number of the pixels in the image, a patch centered around a member of the threshold number of pixels, where a member of the threshold number of pixels is selected based on a pCR predictability level of the pixel, where a pixel having a higher pCR predictability level is more likely to be selected than a pixel having a lower pCR predictability level.

7. The non-transitory computer-readable storage device of claim 1, where a patch has dimensions of 65 pixels by 65 pixels.

8. The non-transitory computer-readable storage device of claim 1, where the CNN is a six block CNN.

9. The non-transitory computer-readable storage device of claim 8, where a block has a convolution layer having batch normalization and a rectified linear unit (ReLU).

10. The non-transitory computer-readable storage device of claim 9, where the CNN employs a multinomial logistic objective loss function for optimization during training.

11. The non-transitory computer-readable storage device of claim 9, where the CNN employs a softmax function to compute the localized patch probability.

12. The non-transitory computer-readable storage device of claim 1, where classifying the region of tissue as a responder or non-responder based, at least in part, on the distribution of predictions across analyzed patches, includes classifying the region of tissue using a majority voting scheme.

13. The non-transitory computer-readable storage device of claim 1, the operations further comprising:
    generating a probability mask based on the pixel-level localized patch probability;
    generating a heatmap based on the probability mask; and
    displaying the probability mask or the heatmap.

14. An apparatus for predicting pathological complete response (pCR) to neoadjuvant chemotherapy (NAC), the apparatus comprising:
    a processor;
    a memory configured to store a radiological image of a region of tissue demonstrating breast cancer, the radiological image having a plurality of pixels, a pixel having an intensity;
    an input/output (I/O) interface;
    a set of circuits; and
    an interface that connects the processor, the memory, the I/O interface, and the set of circuits, the set of circuits comprising:
    an image acquisition circuit configured to:
        access a pre-neoadjuvant chemotherapy (NAC) radiological image of a region of tissue demonstrating breast cancer pathology, the region of tissue including a tumoral region, the image having a plurality of pixels, a pixel having an intensity;
    a patch extraction circuit configured to:
        extract a set of patches from the tumoral region;
    a pCR probability circuit configured to:
        compute a pixel-level pCR probability that the region of tissue will experience pathological complete response (pCR) post-NAC based, at least in part, on the set of patches;
    a classification circuit configured to:
        generate a classification of the region of tissue as a responder or non-responder based, at least in part, on the pixel-level pCR probability, wherein the classification circuit is configured to generate the classification using a majority voting scheme; and
    a display circuit configured to:
        display the classification.

15. The apparatus of claim 14, where the pre-NAC radiological image is a post-contrast dynamic contrast enhanced magnetic resonance imaging (DCE-MRI) image acquired using a 1.5 T or 3 T magnet and a four-channel or eight-channel MRI coil, the pre-NAC radiological image having dimensions of 512 pixels by 512 pixels.

16. The apparatus of claim 14, where the patch extraction circuit is configured to:
for each pixel in the tumoral region, extract a patch centered on each pixel, respectively; or
for a threshold number of pixels in the tumoral region, where the threshold number of pixels is less than number of pixels in the tumoral region, extract a patch centered on each of the threshold number of pixels, respectively, where a member of the threshold number of pixels is selected based on a pCR predictability level of the pixel.

17. The apparatus of claim 14, where the pCR probability circuit is configured as a convolutional neural network, the CNN having six blocks;
where a block has a convolution layer having batch normalization and a rectified linear unit (ReLU);
where the CNN employs a multinomial logistic objective loss function for optimization during training; and
where the CNN computes the pixel-level pCR probability using a softmax function.

18. The apparatus of claim 14, where the image acquisition circuit is further configured to:
access a second pre-NAC radiological image of the region of tissue, where the second pre-NAC radiological image is a pre-contrast DCE-MRI image; and
the set of circuits further comprising a pre-processing circuit configured to:
normalize the pre-NAC radiological image by normalizing the intensity of a pixel in the pre-NAC radiological image to the mean intensity of a reference region of the second pre-NAC radiological image, where the reference region includes a stroma region represented in the second pre-NAC radiological image.

19. The apparatus of claim 14, the set of circuits further comprising:
a heatmap circuit configured to:
generate a pixel-wise probability mask based on the pixel-level pCR probability; and
generate a heatmap of likelihood of response to NAC based, at least in part, on the pixel-wise probability mask and the pre-NAC radiological image; and
where the display circuit is further configured to display the pixel-wise probability mask or the heatmap.

20. A non-transitory computer-readable storage device storing computer-executable instructions that when executed control a computer to perform a method of predicting pathological complete response (pCR) to neoadjuvant chemotherapy (NAC) from baseline breast radiological imagery, the method comprising:
accessing a pre-contrast dynamic contrast enhanced magnetic resonance imaging (DCE-MRI) pre-NAC image of a region of tissue demonstrating breast cancer pathology, the region of tissue including a tumoral region, the pre-contrast DCE-MRI image having a plurality of pixels, a pixel having an intensity;
accessing a post-contrast DCE-MRI pre-NAC image of the region of tissue, the post-contrast DCE-MRI image having a plurality of pixels, a pixel having an intensity;
generating a normalized image by normalizing the post-contrast DCE-MRI image to the mean intensity of a reference region of the pre-contrast DCE-MRI image;
extracting a set of patches from the tumoral region represented in the normalized image, where a patch is centered on a member of a set of pixels, where a member of the set of pixels is selected based on a pCR predictiveness of the member of the set of pixels;
providing the set of patches to a convolutional neural network (CNN) configured to discriminate tissue that will experience pCR post-NAC from tissue that will not experience pCR post-NAC;
receiving, from the CNN, a pixel-level localized patch probability of pCR, where the CNN computes the pixel-level localized patch probability based, at least in part, on the set of patches;
computing a distribution of predictions across analyzed patches based on the pixel-level localized patch probability of pCR;
classifying the region of tissue as a responder or non-responder based, at least in part, on a majority voting scheme applied to the distribution of predictions across analyzed patches; and
displaying the classification.

21. The method of claim 20, further comprising:
generating a probability mask of the tumoral region based on the pixel-level localized patch probability;
generating a heatmap of likelihood of response to NAC based on the probability mask and the normalized image; and
displaying the probability mask or the heatmap.

* * * * *